United States Patent [19]

Kane et al.

[11] 4,286,106

[45] * Aug. 25, 1981

[54] N-[ω-(DIMETHYLAMINO)ALKYL]-3',4'-DICHLOROPROPIONANILIDES

[75] Inventors: Michael P. Kane; Jacob Szmuszkovicz, both of Kalamazoo, Mich.

[73] Assignee: The Upjohn Company, Kalamazoo, Mich.

[*] Notice: The portion of the term of this patent subsequent to Dec. 25, 1996, has been disclaimed.

[21] Appl. No.: 61,569

[22] Filed: Jul. 30, 1979

Related U.S. Application Data

[63] Continuation-in-part of Ser. No. 934,239, Aug. 16, 1978, Pat. No. 4,180,522, which is a continuation of Ser. No. 838,767, Oct. 3, 1977, abandoned, which is a continuation of Ser. No. 746,863, Dec. 2, 1976, abandoned.

[51] Int. Cl.$^3$ ............................................ C07C 103/75
[52] U.S. Cl. ................................... 564/220; 424/324; 564/190; 564/207
[58] Field of Search ...................... 260/557 R, 562 R; 564/190, 207, 220

[56] References Cited

U.S. PATENT DOCUMENTS

| | | | |
|---|---|---|---|
| 2,944,081 | 7/1960 | Wright et al. | 260/562 P |
| 3,016,382 | 1/1962 | Wright et al. | 260/562 R |
| 3,234,276 | 2/1966 | Petracek | 260/558 P |
| 3,573,320 | 3/1971 | Jansen et al. | 260/305 |

*Primary Examiner*—Arthur P. Demers
*Attorney, Agent, or Firm*—Robert A. Armitage

[57] ABSTRACT

The present invention relates to novel organic compounds, useful as antidepressant agents. Further provided are novel methods for the preparation of these compounds and pharmaceutical compositions and methods of use. Particular compounds comprising an aspect of the present invention are N-[ω-(dimethylamino)alkyl]-3',4'-dichloropropionanilides.

9 Claims, No Drawings

N-[ω-(DIMETHYLAMINO)ALKYL]-3',4'-DICHLOROPROPIONANILIDES

DESCRIPTION

CROSS REFERENCE TO RELATED APPLICATION

The present application is a continuation-in-part application of U.S. Ser. No. 934,239, filed Aug. 16, 1978, now U.S. Pat. No. 4,180,522; which is a continuation application of U.S. Ser. No. 838,767, filed Oct. 3, 1977, now abandoned; which is a continuation application of U.S. Ser. No. 746,863, filed Dec. 2, 1976, now abandoned.

TECHNICAL FIELD

The present invention relates to novel organic compounds, useful as antidepressant agents. Further provided are novel methods for the preparation of these compounds and pharmaceutical compositions and methods of use.

Particular compounds comprising an aspect of the present invention are N-[ω-(dimethylamino)alkyl]-3',4'-dichloropropionanilides.

PRIOR ART

Analgesic agents related to the compounds of the instant invention are described in U.S. Pat. Nos. 2,994,081 and 3,016,382.

SUMMARY OF THE INVENTION

The present invention relates to novel antidepressant agents, their methods of preparation, their pharmaceutical compositions, and their methods of use in the treatment of humans. The essential material constituting a disclosure of the above subject matter is incorporated here by reference from U.S. Ser. No. 934,239, filed Aug. 16, 1978, now pending issuance as a United States patent.

Particularly provided by the present invention are:

(a) a compound of formula I

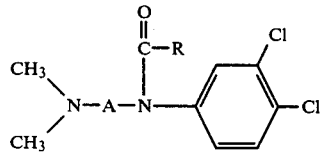

wherein A is alkylene of 4 to 5 carbon atoms, inclusive;
wherein R is ethyl, cyclopropyl or vinyl, or the pharmacologically acceptable acid addition salts thereof;

(b) a compound of formula II

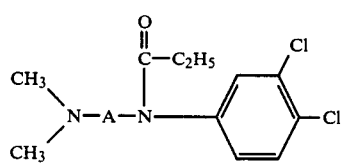

wherein A is alkylene of 4 to 5 carbon atoms, inclusive, or the pharmacologically acceptable acid addition salts thereof; or (c) a compound of formula III

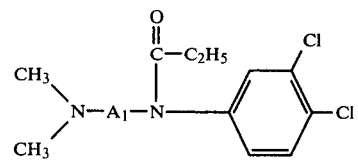

wherein $A_1$ is tetramethylene or pentamethylene or the pharmacologically acceptable acid addition salts thereof.

Examples of alkylene of 4 to 5 carbon atoms are —CH(CH$_3$)—(CH$_2$)$_2$—, —CH$_2$—CH(CH$_3$)—CH$_2$—, —(CH$_2$)$_2$—CH(CH$_3$)—, —(CH$_2$)$_4$, or —(CH$_2$)$_5$—.

DESCRIPTION OF THE PREFERRED EMBODIMENTS

The compounds of the instant invention all represent surprisingly and unexpectedly improved antidepressant agents as compared to the structurally related analgesic agents of the prior art. This surprising and unexpected improvement in pharmacological effects is apparent from the comparative biological effects obtained as follows:

Example 1

Analgesic and Antidepressant Testing

These tests, all performed on Sprague Dawley rats or Carworth Farms mice (CF$_1$) with the above compounds, were undertaken employing the following procedures:

I. ANTIDEPRESSANT TESTS

A. Antagonism of Oxotremorine Hypothermia

Groups of four male CF$_1$ mice (18–22 g each) are injected intraperitoneally with the test compound prepared in 0.25% methylcellulose and placed in plastic cages (15.25 cm×28 cm×12.7 cm). Thirty minutes later, oxotremorine hydrochloride is injected subcutaneously at 1 mg/kg after which mice are placed in a refrigerator maintained at 19° C. A control grup of mice injected with oxotremorine alone is similarly housed. Thirty minutes after the administration of oxotremorine, the intraperitoneal temperature is taken using a thermistor probe. A compound is considered to have antagonized oxotremorine if the body temperature is more than two standard deviations above the body temperature of the control group which received oxotremorine alone. Active compounds are retested using multiple dose levels at 0.3 log intervals. ED$_{50}$'s (50% effective doses) are calculated by the method of Spearman and Karber, Finney, D. F., Statistical Method in Biological Assay, Hafner Publ. Co., N.Y., p. 524 (1952).

B. Apomorphine Gnawing Potentiation

Mice injected with apomorphine at 20 mg/kg subcutaneously or higher are observed to respond by gnawing the paper at the bottom of their cages in a dose related fashion. Lower doses (10 mg/kg, subcutaneously) of apomorphine elicit this response only if the mice are pretreated with antidepressant or stimulant agents. Groups of four (4) albino mice (CF$_1$; 18–22 g each) are injected intraperitoneally with the test compound prepared in 0.25% methylcellulose. One hour later apomorphine hydrochloride is injected subcutaneously at 10 mg/kg. The mice are then placed singly in plastic boxes (10 cm×10 cm×12.7 cm) and observed 30 minutes later for stereotyped gnawing and licking. $ED_{50}$'s are then determined as in the oxotremorine antagonism test.

C. Potentiation of Yohimbine Toxicity in Aggregated Mice

Groups of four (4) albino $CF_1$ mice, weighing 18–22 g each, are injected intraperitoneally with the test compound in 0.25% methylcellulose 30 minutes before challenge with yohimbine HCl at 20 mg/kg intraperitoneally. Each group of mice is then placed in a plastic cage (15.25 cm×28 cm×12.7 cm) and placed in a 30° chamber. A compound is considered active if at least three of the four mice are dead after two hours aggregation. Active compounds are retested at dose levels decreasing at 0.3 log intervals and the number of deaths is used to calculate the $ED_{50}$ by the method of the oxotremorine antagonism test.

II. ANALGESIC TESTS

A. Antagonism of HCl-Induced Writhing

Groups of four (4) male albino $CF_1$ mice (18–22 g each) are injected subcutaneously with the test agent prepared in 0.25% methylcellulose. Thirty minutes later, mice are challenged with a 0.15% HCl solution administered intraperitoneally at 10 ml/kg. Mice are then placed in separate plastic boxes (10 cm×10 cm×12.7 cm) and observed over the following 15 minutes for writhing. A compound is considered active if at least three animals in the group are protected from writhing. $ED_{50}$'s are then calculated as in the antidepressant tests.

B. Antagonism of Air-Induced Writhing

Groups of six (6) male Sprague-Dawley rats (120–150 g each) are injected subcutaneously with the test agent prepared in solution or suspension (100 mg/ml). Immediately thereafter rats are challenged with 7 ml of air administered intraperitoneally. Rats are then placed in separate plastic boxes (10 cm×10 cm×12.7 cm) and observed over the following 15 minutes for writhing. A compound is considered active if at least three animals in the group are protected from writhing. $ED_{50}$'s are then calculated as in the antidepressant tests.

With respect to the above tests, those indicated above to be "ANTIDEPRESSANT TESTS" are known to be standard and recognized animals tests for assessing the antidepressant effects of chemical compounds and, likewise, those tests identified above as "ANALGESIC TESTS" are likewise efficient means for assessing the analgesic potential of chemical compounds. The results of these tests for the compounds of Table I are reported in Table II. From the test data in Table II, CLAIMED COMPOUNDS are all indicated significant and highly potent antidepressants, but fail to exhibit significant analgesic activity. The PRIOR ART COMPOUND shows modest analgesic activity only and is essentially inactive or of a very low order of activity as an antidepressant agent, based on these standard tests.

TABLE I

A. PRIOR ART COMPOUND

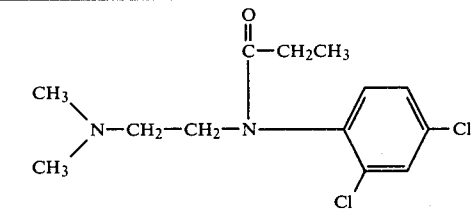

IV

B. CLAIMED COMPOUNDS

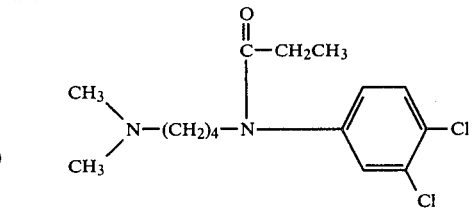

V

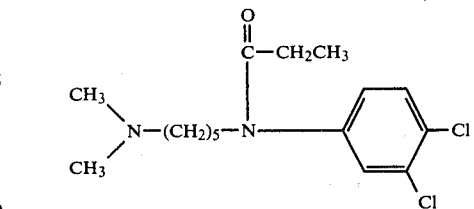

VI

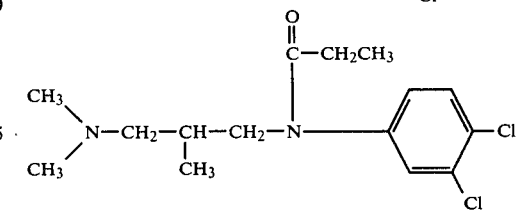

VII

TABLE II

|  | Antidepressant Activity $(ED_{50})^1$ | | | Analgesic Activity $(ED_{50})^1$ | |
|---|---|---|---|---|---|
|  | Yohimbine Toxicity | Oxotremorine Hypothermia | Apomorphine Gnawing | Air-Induced Writhing | HCl-Induced Writhing |
| A. PRIOR ART COMPOUND |  |  |  |  |  |
| IV | 5.0 | >50 | >50 | 50 | 40 |
| B. CLAIMED COMPOUNDS |  |  |  |  |  |
| V | 0.3 | 0.8 | 30.0 | >200 | >50 |
| VI | 1.0 | 4.0 | 20.0 | >200 | >50 |
| VII | 1.0 | 1.0 | 30.0 | >200 | 40 |
| Average | 0.8 | 1.9 | 26.7 | >200 | 200 |
| Average % increase in activity of CLAIMED COMPOUND over PRIOR ART COMPOUNDS | | | | | |
| COMPOUND | 650% | >2500% | >175% | (>400%)[2] | N/A[3] |
| Conclusion: | The CLAIMED COMPOUNDS are dramatically more potent antidepressant agents with equipotent or reduced analgesic effects as compared to the PRIOR ART COMPOUND | | | | |

[1] mg/kg
[2] Decrease in activity
[3] Not applicable

We claim:
1. A compound of formula I

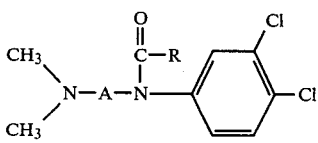

wherein A is alkylene of 4 to 5 carbon atoms, inclusive;

wherein R is ethyl, cyclopropyl or vinyl, or the pharmacologically acceptable acid addition salts thereof.

2. A compound according to claim 1 of formula II

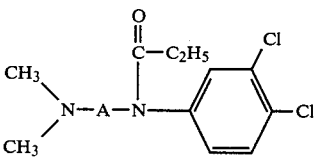

wherein A is alkylene of 4 to 5 carbon atoms, inclusive, or the pharmacologically acceptable acid addition salts thereof.

3. A compound according to claim 2 of formula III

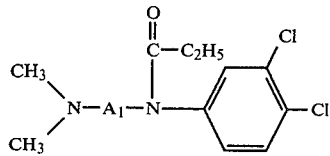

wherein $A_1$ is tetramethylene or pentamethylene or the pharmacologically acceptable acid addition salts thereof.

4. A compound according to claim 3, wherein $A_1$ is tetramethylene, N-[4-(dimethylamino)butyl]-3',4'-dichloropropionanilide.

5. The hydrochloride of the compound of claim 4.

6. A compound according to claim 3, wherein $A_1$ is pentamethylene, N-[5-(dimethylamino)pentyl]-3',4'-dichloropropionanilide.

7. The hydrochloride of the compound of claim 6.

8. A compound according to claim 2, wherein A is —CH$_2$—CH(CH$_3$)—CH$_2$—, N-[(3-dimethylamino)-2-methyl-propyl]-3',4'-dichloropropionanilide.

9. The hydrochloride of the compound of claim 8.

* * * * *

UNITED STATES PATENT OFFICE
CERTIFICATE OF CORRECTION

Patent No. 4,286,106           Dated  25 August 1981

Inventor(s)  Michael P. Kane, et al.

It is certified that error appears in the above-identified patent and that said Letters Patent are hereby corrected as shown below:

Column 3-4, at about line 61, in the column for "Air-Induced Writhing":

```
"    >200                    --    >200
     >200                          >200
     >200     should read          >200
     >200                          >200
      200    "                     >200    -- .
```

Signed and Sealed this

Tenth Day of November 1981

[SEAL]

Attest:

GERALD J. MOSSINGHOFF

Attesting Officer       Commissioner of Patents and Trademarks